US011883523B2

(12) United States Patent
Kalahasti et al.

(10) Patent No.: US 11,883,523 B2
(45) Date of Patent: *Jan. 30, 2024

(54) PLANT EXTRACTS TO REDUCE THE APPEARANCE OF HYPERPIGMENTED SKIN OR TO LIGHTEN SKIN

(71) Applicant: Mary Kay Inc., Addison, TX (US)

(72) Inventors: Geetha Kalahasti, Plano, TX (US); David Gan, Southlake, TX (US)

(73) Assignee: MARY KAY INC., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/575,010

(22) Filed: Sep. 18, 2019

(65) Prior Publication Data

US 2020/0085726 A1 Mar. 19, 2020

Related U.S. Application Data

(60) Provisional application No. 62/732,688, filed on Sep. 18, 2018.

(51) Int. Cl.
| | | |
|---|---|---|
| *A61K 8/9789* | (2017.01) | |
| *A61Q 19/02* | (2006.01) | |
| *A61K 8/06* | (2006.01) | |
| *A61K 8/9711* | (2017.01) | |

(52) U.S. Cl.
CPC ............ *A61K 8/9789* (2017.08); *A61K 8/062* (2013.01); *A61K 8/9711* (2017.08); *A61Q 19/02* (2013.01)

(58) Field of Classification Search
None
See application file for complete search history.

(56) References Cited

U.S. PATENT DOCUMENTS

| | | |
|---|---|---|
| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,087,445 A | 2/1992 | Haffey et al. |
| 5,100,660 A | 3/1992 | Hawe et al. |
| 5,262,153 A | 11/1993 | Mishima et al. |
| 5,411,741 A | 5/1995 | Zaias |
| 6,162,458 A | 12/2000 | Asada et al. |
| 7,419,688 B2 | 9/2008 | Perrier et al. |
| 8,426,381 B2 | 4/2013 | Thibodeau et al. |
| 8,652,536 B2 | 2/2014 | Da Luz Moreira et al. |
| 9,579,279 B2 | 2/2017 | Athwal |
| 9,669,012 B2 | 6/2017 | Anderson et al. |
| 2012/0189565 A1 | 7/2012 | da Luz Moreira et al. |
| 2015/0056255 A1 | 2/2015 | Ragot et al. |
| 2016/0008270 A1 | 1/2016 | Gan et al. |
| 2016/0324762 A1* | 11/2016 | Vepuri ................... A61K 8/735 |
| 2017/0000714 A1 | 1/2017 | Hwang et al. |

FOREIGN PATENT DOCUMENTS

| | | |
|---|---|---|
| BR | PI0605812 | 8/2008 |
| CN | 107375048 | 11/2017 |
| CN | 107468585 | 12/2017 |
| CN | 108309825 | 7/2018 |
| CN | 108324601 | 7/2018 |
| JP | 2001322941 | 11/2001 |
| JP | 2013103927 | 5/2013 |
| KR | 1020060106310 | 10/2006 |
| KR | 100848800 | 7/2008 |
| WO | WO 2016164460 | 10/2016 |

OTHER PUBLICATIONS

Longhini et al (Revista Brasileira de Farmacognosia 27:254-271, 2017) (Year: 2017).*
Gendler (Aesthetic Surg J 25:618-624, 2005) (Year: 2005).*
Basit et al (StatPearls, 2021—available online at https://www.ncbi.nlm.nih.gov/books/NBK459271/) (Year: 2021).*
Kang et al (Ann Dermatol 22(4):373-378, 2010) (Year: 2010).*
Bandyopadhyay (Indian J Dermatol, 54:303-309, 2009) (Year: 2009).*
Eberlin et al (J Cosmetic Dermatology 8:127-135, 2008) (Year: 2008).*
*Adipolin—preliminary report.* Barnet.
*Adipolin Schinus terebnthifolius Seed Extract.* Barnet.
International Search Report and Written Opinion issued in corresponding application No. PCT/US2019/051719, dated Dec. 30, 2019.
Jorge et al., "Schinus terebinthifolius Raddi extract and linoleic acid from Passiflora edulis synergistically decrease melanin synthesis in B16 cells and reconstituted epidermis" *International Journal of Cosmetic Science* 2012, 34, 435-440, 435, 438-439.
Packman et al., "Topical moisturizers: quantification of their effect on superficial facial lines" *J. Soc. Cosmet. Chem.* 1978, 29, 79-90.
*Slendyl® Reshapes the silhouette & Prevents the loss of firmness for a perfect body.* Gelyma.
*Slimbuster H: The Natural Tonic from the Amazon Anti-cellulite agent Draining and microcirculation normalization.* Chemyunion Quimica LTDA.
Eberlin, et al. "Effects of a Brazilian herbal compound as a cosmetic eyecare for periorbital hyperchromia ("dark circles")" *Journal of Cosmetic Dermatology* 8, pp. 127-135, 2009.

(Continued)

*Primary Examiner* — Craig D Ricci

(74) *Attorney, Agent, or Firm* — NORTON ROSE FULBRIGHT US LLP

(57) ABSTRACT

A method for reducing the appearance of hyperpigmented skin is disclosed. The method can include topically applying to hyperpigmented skin of a person a composition that includes at least one of, at least two of, or all three of (i) an effective amount of *Schinus terebinthifolius* seed extract, (ii) an effective amount of a mixture comprising *Ptychopetalum olacoides* bark/stem extract, *Pfaffia paniculata* root extract, and *Trichilia catigua* bark extract, and/or (iii) an effective amount of a mixture comprising *Himanthalia elongata* extract and *Undaria pinnatifida* extract. Topical application of the composition can reduce the appearance of the hyperpigmented skin.

10 Claims, No Drawings

(56) References Cited

OTHER PUBLICATIONS

Extended European Search Report issued in corresponding European Application No. 19863071.7, dated May 18, 2022.
Gottschalck T et al. "International Cosmetic Ingredient Dictionary and Handbook", International Cosmetic Ingredient Dictionary and Handbook, Jan. 1, 2004, pp. 1669-1670, XP002380579 *the whole document*.
Database GNPD [Online] Mintel: Jan. 30, 2017, anonymous: "Marine Complex Deep Restorative Cream", XP055909202, Database accession No. 4580477 *ingredients list*.
Jorge A T S et al: "Schinus terebinthifolius Raddi extract and linoleic acid from Passiflora edulis synergistically decrease melanin synthesis in B16 cells and reconstituted epidermis", International Journal of Cosmetic Science, Kluwer Academic Publishers, Dordrecht, NL, vol. 34, No. 5, Jul. 21, 2012, pp. 435-440, XP071469936, ISSN: 0142/5463, DOI: 10.1111/ J. 1468-2494. *p. 436, left-hand column, paragraph third-right-hand column, paragraph first* *p. 439, right-hand column, paragraph third*.
Database WPI Week 200918 Thomson Scientific, London, GB; AN 2009-B48145 XP 002806408.
Kim Min-Jin et al: "Melanogenesis inhibitory activity of Korean Undaria pinnatifida in mouse B16 melanoma cells", Interdisciplinary Toxicology, vol. 7, No. 2, Jun. 1, 2014, pp. 89-92 *abstract*.
Longhini et al., "Trichilia catigua: therapeutic and cosmetic values" *Revista Brasileira de Farmacognosia* 2017, 27, pp. 254-271.
Office Action and Search Report issued in Corresponding Chinese Application No. 201980061260.0, dated Jun. 6, 2023 (English Translation provided).
Xie, Wenying. *Complete Collection of Meridian and Acupoint Massage*. Shaanxi Science and Technology Press, 2018, p. 348 (English Translation of relevant parts provided).
"~H2O+ Green Tea Antioxidant Eye Serum." H2O Plus, L.P., GZBJZ No. J20127156, 4 pages, *National Medical Products Administration* (English Translation of relevant parts provided).
"Givenchy L 'Intemporel Blossom Beautifying Radiance Serum." LVMH Fragrance Brands, GZBJZ No. J20180471, 5 pages, *National Medical Products Administration* (English Translation of relevant parts provided).
Office Action and Search Report issued in Corresponding Chinese Application No. 201980061260.0, dated Nov. 11, 2022 (English Translation provided).
Wang, Jianxin. *Collection of Cosmetic Plant Materials*. China Textile Press, 2012, pp. 411-412 (English Translation of relevant parts provided).

* cited by examiner

PLANT EXTRACTS TO REDUCE THE APPEARANCE OF HYPERPIGMENTED SKIN OR TO LIGHTEN SKIN

CROSS-REFERENCE TO RELATED APPLICATIONS

This application claims the benefit of U.S. Provisional Application No. 62/732,688 filed Sep. 18, 2018. The contents of the referenced application are incorporated into this application by reference.

BACKGROUND OF THE INVENTION

A. Field of the Invention

The present invention relates generally to topical skin compositions and methods that can be used to lighten/whiten skin, even out skin tone, and/or treat hyperpigmented skin. In particular, the compositions can include plant based materials selected from *Schinus terebinthifolius* seed extract, *Ptychopetalum olacoides* bark/stem extract, *Pfaffia paniculata* root extract, *Trichilia catigua* extract, *Himanthalia elongata* extract, or *Undaria pinnatifida* extract, or any combination thereof, to lighten skin, even out skin tone, or treat hyperpigmentation.

B. Background

Ageing, chronic exposure to adverse environmental factors, malnutrition, fatigue, etc., can change the visual appearance, physical properties, and/or physiological functions of skin and tissue in ways that are considered visually undesirable. The most notable and obvious changes include the development of fine lines and wrinkles, loss of elasticity, increased sagging, loss of firmness, loss of color evenness or even skin tone, coarse surface texture, and mottled pigmentation.

With respect to loss of color evenness or even skin tone and mottled pigmentation, this can be caused by increased melanin production, which can result in hyperpigmented skin. In particular, coloring in human skin is caused by melanin. Melanin is produced in special dendritic cells, melanocytes, which are found below or between the basal cells of the epidermis of the skin (U.S. Pat. No. 5,411,741). Melanin is synthesized by a reaction cascade triggered by the enzyme tyrosinase (U.S. Pat. No. 5,262,153) where tyrosine is converted into melanin. Over production of melanin can result in hyperigmented skin such as skin having pigmentary variation or abnormal pigmentation of the skin. This may present on the skin as unwanted freckles or as senile lentigo. Senile lentigo is commonly referred to as dark spots, age spots, liver spots, or solar lentigo. Other types of hyperpigmentation include melasmic skin, post-inflammatory hyperpigmentation due to abrasion, burns, wounds or dermatitis, acne, or phototoxic reaction and other similar small, fixed pigmented lesions.

Exposure to extrinsic factors such as ultra violet (UV) radiation from the sun, skin irritants, and/or pollution, can trigger the biochemical pathways leading to increased melanin production and ultimately to hyperpigmented skin and uneven skin tone. Still further, hormonal changes can also trigger these biochemical pathways and lead to hyperpigmented skin and uneven skin tone such as melasma. By way of example, keratinocytes (outermost cells of the skin) can release signaling molecules, such as α-melanocyte-stimulating hormone (α-MSH) and inflammatory cytokines, each of which can lead to increased melanin production by melanocytes. It is often desirable to lighten these hyperpigmented areas or even out the appearance of irregularly pigmented areas of skin to provide a more even looking skin tone/skin color. Individuals may also wish to increase fairness of or reduce the overall level of pigmentation in the skin. In either case, hyperpigmentation or uneven skin tone are each usually viewed as cosmetically undesirable.

Conventional depigmenting agents, such as hydroquinone, corticosteroids, and kojic acid can raise several safety concerns (e.g., ochronosis, atrophy, carcinogenesis, and other local or systemic side effects) with long-term exposure. In some instances, the use of one skin lightening ingredient may not be effective for individuals with significant hyperpigmentation, freckles, or age spots, for example. Additionally, previous attempts to combine various skin lightening ingredients have been ineffective, and in some instances, have produced negative results such as exasperating the production of inflammatory cytokines, irritating the skin, prolonging recovery periods, and/or inefficient delivery of the promised benefits.

While there have been attempts to produce more natural-based ingredients, such attempts oftentimes require several ingredients and/or do not provide a sufficient level of efficacy. By way of example, Korean Publication 10-2005-0028920 discloses the use of a rinse-off soap to wash and whitening skin. The soap includes mung beans, brown rice, adlay, white corvania (*baektae*) (i.e., soybean or *Glycine max L. Merr.*), dried *Artemisia* leaves, dried peach seeds, silkworms killed by white muscardine disease, *sangyak*, *Houttuynia cordata*, dried dodder seeds, orange peels, green tea leaves, sea mustard, kelp, and buckwheat.

Thus, previous attempts to improve skin tone or lighten skin have been shown to have various drawbacks such as high costs, medical risks, skin irritation, prolonged recovery periods, or inefficient delivery of the promised skin benefits.

SUMMARY OF THE INVENTION

The inventors have identified a solution to at least some of the problems associated with treating hyperpigmented skin, whitening or lighting skin, and/or evening out skin tone color. The solution resides in the discovery of plant-based ingredients that can effectively treat these skin conditions and/or produce these results. In particular, the inventors have discovered that any one of the following, any combination of the following, or all of the following plant-based extracts can reduce the appearance of hyperpigmented skin, whiten or lighten skin, or even out skin tone color: *Schinus terebinthifolius* seed extract; *Ptychopetalum olacoides* bark/stem extract; *Pfaffia paniculata* root extract; *Trichilia catigua* extract; *Himanthalia elongata* extract; and/or *Undaria pinnatifida* extract. In some instances, a mixture comprising *Ptychopetalum olacoides* bark/stem extract, *Pfaffia paniculata* root extract, and *Trichilia catigua* extract can be used in whitening or lightening skin formulations and corresponding methods of use. In some instances, a mixture comprising *Himanthalia elongata* extract and *Undaria pinnatifida* extract can be used in whitening or lightening skin formulations and corresponding methods of use.

In one aspect of the present invention, there is disclosed a method for reducing the appearance of hyperpigmented skin in a person or whitening or lightening a person's skin. In the context of the present invention, whitening and lightening can be used interchangeably and can encompass the production of less melanin when compared with not using the compositions of the present invention on skin. The method can include topically applying to hyperpigmented skin of the person or skin desiring to be made lighter a composition that includes at least one of, at least two of, or all three of: (i) an effective amount of *Schinus terebinthifolius* seed extract; (ii) an effective amount of a mixture comprising *Ptychopetalum olacoides* bark/stem extract, *Pfaffia paniculata* root extract, and *Trichilia catigua* extract; or (iii) an effective amount of a mixture comprising *Himanthalia elongata* extract and *Undaria pinnatifida* extract. Topical application of the composition can reduce the hyperpigmented skin and/or lighten the person's skin. In other aspects, however, the mixtures in (ii) and (iii) do not have to be used; rather the individual ingredients can be used and any combination of the extracts of the present invention can be used in the methods and compositions of the present invention. However, in one aspect of the present invention, the mixture (ii) can include *Ptychopetalum olacoides* bark/stem extract, *Pfaffia paniculata* root extract, and *Trichilia catigua* extract along with water, butylene glycol, and PEG-40 hydrogenated castor oil. In another aspect, the mixture (iii) can include *Himanthalia elongata* extract and *Undaria pinnatifida* extract along with water. In some instances, the compositions of the present invention can include at least two of (i), (ii), and (iii). In some instances, the composition can include all three of (i), (ii), and (iii). In some aspects, the hyperpigmented skin can be melasmic skin. In some aspects, the hyperpigmented skin can be or senile lentigo, which can also be referred to as dark spots, age spots, liver spots, or solar lentigo. Thus, the compositions of the present invention can be used to treat age-related hyperpigmentation such as senile lentigo, which oftentimes presents on the skin after prolonged exposure to UV radiation or chemicals and other pollutants found in air and/or compositions applied to skin. In some instances, the compositions of the present invention can be used on people that are at least 20 years old, preferably at least 30 years old, more preferably at least 40 years old, and even more preferably at least 50 or at least 60 years old or more.

Also disclosed in the context of the present invention is a topical skin composition comprising at least one of, at least two of, at least three of, at least four of, at least five of, or all six of *Schinus terebinthifolius* seed extract, *Ptychopetalum olacoides* bark/stem extract, *Pfaffia paniculata* root extract, *Trichilia catigua* extract, *Himanthalia elongata* extract, and *Undaria pinnatifida* extract, wherein the composition is capable of reducing the appearance of hyperpigmented skin on a person. In some aspects, and as noted above, the composition can include at least one of, at least two of, or all three of: (i) an effective amount of *Schinus terebinthifolius* seed extract; (ii) an effective amount of a mixture comprising *Ptychopetalum olacoides* bark/stem extract, *Pfaffia paniculata* root extract, and *Trichilia catigua* extract; or (iii) an effective amount of a mixture comprising *Himanthalia elongata* extract and *Undaria pinnatifida* extract.

In some instances, the hyperpigmented skin or skin having uneven skin tone color is located on facial skin such as the forehead, cheeks, nose, chin, the orbital region of skin (e.g., under the eye, eyelids, adjacent to the eye where crows fee form, etc.), or the eyebrows. Alternatively, the hyperpigmented skin or skin having uneven skin tone color is located on non-facial skin (e.g., hands, thighs, neck, buttocks, dècoletè region, feet, etc.). Thus, it is contemplated in the context of the present invention that the compositions can be applied to facial skin or non-facial skin.

The extracts used in the compositions of the present invention can each individually be obtained from water as an extracting solvent (e.g., aqueous extract), alcohol as an extracting solvent (e.g., alcohol extract), or a polyol as the extracting solvent (e.g., polyol extract), or any combinations of such extracting solvents (e.g., aqueous-alcoholic extract, aqueous-polyol extract, alcohol-polyol extract or aqueous-alcoholic-polyol extract). Non-limiting examples of alcohols can be methanol, ethanol, propanol, butanol, petnanol, hexanol, heptanol, octanol, etc. Non-limiting examples of polyols can be ethylene glycol, propylene glycol, glycerol, erythritol, xylitol, mannitol, volemitol, etc. Additionally, other extracting solvents can be used such as additional hydrophilic solvents or lipophilic solvents (e.g., methane, ethane, butane, propane, hexane, heptane, octane, dimethyl sulfoxide (DMSO), N-methyl-2-pyrrolidone (NMP), carbon dioxide such as use of carbon dioxide in supercritical extraction techniques). $CO_2$ supercritical extraction can include filling a column with ground dried plant material and pumping supercritical liquid carbon dioxide though the column at very high pressure (200-400 Bar), and then collecting the resulting extract.

In some instances, the *Schinus terebinthifolius* seed extract can be obtained from the seed portion of *Schinus terebinthifolius*. The seed extract can be prepared by subjecting the seed, preferably in crushed or macerated form, to a super critical extraction process using carbon dioxide ($CO_2$) as the solvent. The supercritical extract of *Schinus terebinthifolius* seed can then be used in the compositions and methods of the present invention. In some instances, the *Ptychopetalum olacoides* bark/stem extract can be obtained from the bark and stem of *Ptychopetalum olacoides*. The bark/stem extract can be prepared by subjecting the bark and stem, preferably in crushed or macerated form, to an aqueous solution (preferably 100% water) using water as the solvent. The aqueous extract of *Ptychopetalum olacoides* bark/stem can then be used in the compositions and methods of the present invention. In some aspects, the *Pfaffia paniculata* root extract can be obtained from the roots of *Pfaffia paniculata*. The root extract can be prepared by subjecting the roots, preferably in crushed or macerated form, to an aqueous solution (preferably 100% water) using water as the solvent. The aqueous extract of *Pfaffia paniculata* root can then be used in the compositions and methods of the present invention. In some aspects, the *Trichilia catigua* extract can be obtained from the bark of *Trichilia catigua*. The *Trichilia catigua* bark extract can be prepared by subjecting the bark, preferably in crushed or macerated form, to an aqueous solution (preferably 100% water) using water as the solvent. The aqueous extract of *Trichilia catigua* bark can then be used in the compositions and methods of the present invention. In some aspects, the *Himanthalia elongata* extract can be obtained from the whole plant/algae of *Himanthalia elongata*. The whole algae plant extract of *Himanthalia elongata* can be prepared by subjecting the entire algae plant, preferably in crushed or macerated form, to an aqueous solution (preferably 100% water) using water as the solvent. The aqueous extract of *Himanthalia elongata* whole algae plant can then be used in the compositions and methods of the present invention. In some aspects, the *Undaria pinnatifida* extract can be obtained from the whole plant/algae of *Undaria pinnatifida*. The whole algae plant extract of *Undaria pinnatifida* can be prepared by subjecting the entire algae plant, preferably in crushed or macerated form, to an aqueous solution (preferably 100% water) using water as the solvent. The aqueous extract of *Undaria pinnatifida* whole algae plant can then be used in the compositions and methods of the present invention.

An effective amount of each of the extracts (*Schinus terebinthifolius* seed extract, the *Ptychopetalum olacoides* bark/stem extract, the *Pfaffia paniculata* root extract, the *Trichilia catigua* extract, the *Himanthalia elongata* extract, and/or the *Undaria pinnatifida* extract) or combinations or mixtures of extracts in the compositions of the present invention can be 0.00001 to 25% w/w or any range therein (e.g., 0.00001 to 10% w/w, 0.00001 to 5% w/w, 0.00001 to 2% w/w, 0.00001 to 1% w/w, 0.00001 to 0.5% w/w, or 0.001 to 1% w/w, 0.01 to 1% w/w, 0.1 to 1% w/w. or 0.001 to 2% w/w, 0.01 to 2% w/w, or 0.1 to 2% w/w). In some aspects, an effective amount of each extract can be 0.00001 wt. % to 3 wt. %, preferably, 0.0001 wt. % to 2 wt. %, or more preferably 0.0001 wt. % to 1 wt. %, or even more preferably from 0.0001 wt. % to 0.5 wt. %. Each extract can individually be present in these amounts. Combinations of extracts can be present in these amounts. Mixtures of extracts can be present in these amounts. Mixtures includes a mixture or combination of extracts and optionally other ingredients that form a single ingredient that can then be combined with other ingredients to form a topical skin composition. By comparison, combinations of extracts and optionally other ingredients can each be individual ingredients that can be individually combined with other ingredients to form a topical skin composition.

The extracts (*Schinus terebinthifolius* seed extract, the *Ptychopetalum olacoides* bark/stem extract, the *Pfaffia paniculata* root extract, the *Trichilia catigua* extract, the *Himanthalia elongata* extract, and/or the *Undaria pinnatifida* extract) can reduce melanogenesis. In other instances, the extracts can reduce tyrosinase activity in skin. In other aspects, the extracts can reduce melanogenesis through activation of an adiponectin (Adipo Q) receptor. In some instances, the Adipo Q receptor is PAQR7. Without wishing to be bound by theory, it is believed that each of the extracts or combinations thereof can act as agonists for the PAQR7 receptor, which can then lead to a down regulation of melanocyte production in skin cells. In still another aspect of the present invention, the extracts can increase adiponectin production in the skin.

In addition to the extracts of the preset invention, the topical skin compositions of the present invention can further comprise one or more ingredients described herein. For example, the composition can comprise one or more additional ingredients selected from one or more cosmetic ingredients or pharmaceutical ingredients. In some instances, the compositions can include one or more conditioning agents, moisturizing agents, pH adjusters, structuring agents, silicone containing compounds, inorganic salts, and/or preservatives. In some aspects, the topical composition further includes water, preferably at least 50, 60, 70, 80, or 90, or more wt. % water, more preferably between 50 to 90 wt. % water. In some aspects, the topical compositions of the present invention may exclude one or more additional ingredients selected from one or more cosmetic ingredients or pharmaceutical ingredients. In still some particular aspects, the compositions of the present invention may exclude one or more of *Schinus terebinthifolius* seed extract, the *Ptychopetalum olacoides* bark/stem extract, the *Pfaffia paniculata* root extract, the *Trichilia catigua* extract, the *Himanthalia elongata* extract, and/or the *Undaria pinnatifida* extract. In some aspects, the topical composition excludes water. In some aspects, the topical composition herein may be anhydrous or substantially anhydrous.

In particular aspects, the compositions of the present invention are formulated as a topical skin composition. The composition can have a dermatologically acceptable vehicle or carrier for the compounds and extracts. The composition can further include a moisturizing agent or a humectant, a surfactant, a silicone containing compounds, a UV agent, an oil, and/or other ingredients identified in this specification or those known in the art. The composition can be a mask, lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include sodium benzoate, iodopropynyl butylcarbamate, methylparaben, propylparaben, or a mixture of methylparaben and propylparaben. In some embodiments, the composition is paraben-free.

Compositions of the present invention can have UVA and UVB absorption properties. The compositions can have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a cleansing balm, a toner, a sunscreen, a mask, an anti-aging product, a deodorant, an antiperspirant, a perfume, a cologne, etc.

Also disclosed are the following Embodiments 1 to 20 of the present invention. Embodiment 1 is a method for reducing the appearance of hyperpigmented skin in a person, the method comprising topically applying to hyperpigmented skin of the person a composition that includes at least one of: (i) an effective amount of *Schinus terebinthifolius* seed extract; (ii) an effective amount of a mixture comprising *Ptychopetalum olacoides* bark/stem extract, *Pfaffia paniculata* root extract, and *Trichilia catigua* bark extract; and/or (iii) an effective amount of a mixture comprising *Himanthalia elongata* extract and *Undaria pinnatifida* extract, wherein topical application of the composition reduces the appearance of the hyperpigmented skin. Embodiment 2 is the method of Embodiment 1, wherein the hyperpigmented skin is a senile lentigo and/or melasmic skin. Embodiment 3 is the method of any one of Embodiments 1 to 2, wherein the composition whitens the skin and/or evens out the skin tone. Embodiment 4 is the method of any one of Embodiments 1 to 3, wherein the composition reduces melanogenesis activity in the skin. Embodiment 5 is the method of any one of Embodiments 1 to 4, wherein the composition reduces melanogenesis activity through activation of an adiponectin (Adipo Q) receptor. Embodiment 6 is the method of Embodiment 5, wherein the Adipo Q receptor is PAQR7. Embodiment 7 is the method of any one of Embodiments 1 to 6, wherein the composition comprises the *Schinus terebinthifolius* seed extract. Embodiment 8 is the method of Embodiment 7, wherein the *Schinus terebinthifolius* seed extract is obtained with a supercritical carbon dioxide ($CO_2$) extraction solvent. Embodiment 9 is the method of any one of Embodiments 1 to 8, wherein the composition comprises the mixture comprising *Ptychopetalum olacoides* bark/stem extract, *Pfaffia paniculata* root extract, and *Trichilia catigua* bark extract. Embodiment 10 is the method of Embodiment 9, wherein the mixture further comprises water, butylene glycol, and PEG-40 hydrogenated castor oil. Embodiment 11 is the method of any one of Embodiments 9 or 10, wherein the *Ptychopetalum olacoides* bark/stem extract is an aqueous extract, the *Pfaffia paniculata* root extract is an aqueous extract, and/or the *Trichilia catigua* bark extract is an aqueous extract. Embodiment 12 is the method of any one of Embodiments 1 to 11, wherein the composition comprises the mixture comprising *Himanthalia elongata* extract and *Undaria pinnatifida* extract. Embodiment 13 is the method of Embodiment 12, wherein the mixture further comprises water. Embodiment 14 is the method of any one of Embodiments 12 or 13, wherein the *Himanthalia elongata* extract is an aqueous extract and/or the *Undaria pinnatifida* extract is an aqueous extract, and wherein each extract is from whole algae organism of *Himanthalia elongata* and/or *Undaria pinnatifida*. Embodiment 15 is the method of any one of Embodiments 1 to 14, wherein the composition comprises at least two of (i), (ii), and (iii). Embodiment 16 is the method of Embodiment 15, wherein the composition comprises all three of (i), (ii), and (iii). Embodiment 17 is the method of any one of Embodiments 1 to 16, wherein the composition comprises: 0.00001 to 10% w/w of *Schinus terebinthifolius* seed extract; 0.00001 to 10% w/w of the mixture comprising *Ptychopetalum olacoides* bark/stem extract, *Pfaffia paniculata* root extract, and *Trichilia catigua* bark extract; and/or 0.00001 to 10% w/w of the mixture comprising *Himanthalia elongata* extract and *Undaria pinnatifida* extract. Embodiment 18 is the method of any one of Embodiments 1 to 17, wherein the composition is an emulsion, preferably an oil-in-water emulsion. Embodiment 19 is the method of any one of Embodiments 1 to 18, wherein the composition is a gel. Embodiment 20 is a topical skin composition comprising at least one of, at least two of, or all three of: (i) an effective amount of *Schinus terebinthifolius* seed extract; (ii) an effective amount of a mixture comprising *Ptychopetalum olacoides* bark/stem extract, *Pfaffia paniculata* root extract, and *Trichilia catigua* bark extract; and/or (iii) an effective amount of a mixture comprising *Himanthalia elongata* extract and *Undaria pinnatifida* extract, wherein the composition is capable of reducing the appearance of hyperpigmented skin on a person.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations refer to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

The terms "wt. %," "vol. %," or "mol. %" refers to a weight, volume, or molar percentage of a component, respectively, based on the total weight, the total volume, or the total moles of material that includes the component. In a non-limiting example, 10 grams of component in 100 grams of the material is 10 wt. % of component. The term "% w/w" has the same meaning as wt. %.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is the ability to reduce the appearance of hyperpigmented skin, whiten or light skin, and/or even out skin tone color (i.e., even out skin tone) with at least one or any combination or all of the aforementioned plant based extracts.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Many people in the U.S. and world-wide suffer from hyperpigmentation or uneven skin tone. In many instances, it is often desirable to lighten these discolorations or even out the appearance of the irregularly pigmented areas of skin. Also, and in certain cultures, people correlate lighter skin tone or color with beauty. Therefore, people in these cultures may have a desire to lighten their natural skin color with skin-lightening agents or compounds.

The compositions of the present invention provide for an effective alternative to known methods for treating hyperpigmented skin or evening out skin tone or lightening skin. The discovery does not rely on the use of more traditional chemical compounds such as hydroquinone, corticosteroids, and kojic acid. Rather, the discover pertains to the use of plant-based materials to bring about the desired skin lightening effects. These plant based materials include *Schinus terebinthifolius* seed extract, *Ptychopetalum olacoides* bark/stem extract, *Pfaffia paniculata* root extract, *Trichilia catigua* extract, *Himanthalia elongata* extract, and/or *Undaria pinnatifida* extract, or any combination thereof.

These and other non-limiting aspects of the present invention are described in the following sections.

A. Active Ingredients

The present invention is premised on the inventors' discovery that *Schinus terebinthifolius* seed extract, *Ptychopetalum olacoides* bark/stem extract, *Pfaffia paniculata* root extract, *Trichilia catigua* extract, *Himanthalia elongata* extract, and/or *Undaria pinnatifida* extract can be used to inhibit pigmentation of skin, whiten skin, even out skin tone, and/or treat hyperpigmentation. This can be done through inhibiting melanogenesis in skin cells.

*Schinus terebinthifolius* seed extract is an extract from the seed of a flowering plant of the Anacardiaceae (cashew) family, which is located primarily in subtropical and tropical South America. In some instances, *Schinus terebinthifolius* seed extract is commercially available. In some instances, *Schinus terebinthifolius* seed extract can be supplied by Barnet Products Corporation under the trade name ADIPOLIN™. In a preferred instance, $CO_2$ supercritical extraction can be used to obtain the *Schinus terebinthifolius* seed extract. $CO_2$ supercritical extraction can include filling a column with ground dried plant material and pumping supercritical liquid carbon dioxide though the column at very high pressure (200-400 Bar), and then collecting the resulting extract.

*Ptychopetalum olacoides* bark/stem extract, also known as "marapuama extract," is from the bark and stem of a flowering plant of the Olacaceae family, which is located primarily in the Amazon rainforest. *Pfaffia paniculata* root extract, also known as "suma" extract, is from the root of a flowering plant of the Amaranthaceae (gingseng) family, which is located primarily in subtropical and tropical South America. *Trichilia catigua* extract, also known as "catabu" extract, is from the plant *Trichilia catigua*, which is located primarily in semi-deciduous parts of the Atlantic Forests of South and Central America. In some instances, *Ptychopetalum olacoides* bark/stem extract, *Pfaffia paniculata* root extract, and *Trichilia catigua* extract are commercially available as a mixture. In some instances, this mixture of extracts can be supplied by Chemyunion under the trade name SLIMBUSTER™ H. In other instances, however, it is contemplated that these extracts can be individually used in the context of the present invention rather than as a mixture. In some instances, each of the *Ptychopetalum olacoides* bark/stem, *Pfaffia paniculata* root, and *Trichilia catigua* extracts are aqueous extracts where an aqueous solution (preferably 100% water) is used as the extracting solvent. Ground dried plant material from each plant can be subjected to an aqueous solution at room temperature (e.g., 20°

C. to 30° C.) up to 100° C., and the resulting liquid solution can be obtained. In some instances, the ground dried plant material includes a combination of each of *Ptychopetalum olacoides* bark/stem, *Pfaffia paniculata* root, and *Trichilia catigua* dried plant material. In other instances, separate extracts of each are obtained. The liquid solution (or solutions if individual extracts are prepared) can be used in the context of the present invention. Alternatively, the liquid solution (or solutions if individual extracts are prepared) can be dried to obtain the dried solute material, which can then be used in the context of the present invention. In addition to water, the aqueous extracting solution can include an alcohol (e.g., methanol, ethanol, or propanol, or a mixture thereof), a glycol (e.g., propylene glycol or butylene glycol), glycerin, or combinations thereof.

*Himanthalia elongata* extract, also known as "thong-weed," "sea thong," or "sea spaghetti" extract, is from *Himanthalia elongata* (a brown algae) predominately found in north east Atlantic Ocean and the North Sea. *Undaria pinnatifida* extract, also known as "wakame" extract, is from *Undaria pinnatifida* (a brown algae) predominately found in cold coastal areas of Asia (e.g., Japan, Korea, and China). In some instances, *Himanthalia elongata* extract and *Undaria pinnatifida* extract are commercially available as a mixture. In some instances, this mixture of extracts can be supplied by Biosil Technologies, Inc., under the trade name SLENDYL®. In other instances, however, it is contemplated that these extracts can be individually used in the context of the present invention rather than as a mixture. The extracts are also individually commercially available. In some instances, each of the *Himanthalia elongata* extract and *Undaria pinnatifida* extract are aqueous extracts where an aqueous solution (preferably 100% water) is used as the extracting solvent. Ground dried plant material from each plant can be subjected to an aqueous solution at room temperature (e.g., 20° C. to 30° C.) up to 100° C., and the resulting liquid solution can be obtained. In some instances, the ground dried plant material includes a combination of both *Himanthalia elongata* and *Undaria pinnatifida* dried plant material. In some instances, separate extracts of each are obtained. The liquid solution (or solutions if individual extracts are prepared) can be used in the context of the present invention. Alternatively, the liquid solution (or solutions if individual extracts are prepared) can be dried to obtain the dried solute material, which can then be used in the context of the present invention. In addition to water, the aqueous extracting solution can include an alcohol (e.g., methanol, ethanol, or propanol, or a mixture thereof), a glycol (e.g., propylene glycol or butylene glycol), glycerin, or combinations thereof.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc. In certain instances, each of the extracts can be prepared by: (i) obtaining the desired plant part (e.g., leaf, stem, bark, flower, seed, etc.) or whole plant; (ii) crushing or macerating the plant part or whole plant; (iii) optionally drying the crushed or macerated plant part or whole plant; (iv) subjecting the crushed or macerated plant or plant part to an extraction solvent to a sufficient period of time (e.g., 1, 5, 10, 30, or 45 minutes or more, or 1, 6, 12, or 18 hours or more, or 2, 3, 4, 5, 6 days, or more) under room temperature (e.g., 20 to 30° C.) or heated (e.g., greater than 30° C. or more, preferably 30° C. to less than the boiling point of the solvent); (v) collecting the solution comprising the extracting solvent and the extracted plant material (e.g., liquid extract); and (vi) optionally removing the extracting solvent to obtain a dried plant extract; and (vii) optionally reconstituting the dried plant extract in a liquid carrier (e.g., water, alcohol, diol, etc.). It is also contemplated in the context of the present invention that plant material from each of *Schinus terebinthifolius* seed extract, *Ptychopetalum olacoides* bark/stem extract, *Pfaffia paniculata* root extract, *Trichilia catigua* extract, *Himanthalia elongata* extract, and/or *Undaria pinnatifida* extract, can be directly used without subjecting the plant material to an extraction technique.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of any ingredient within the compositions can vary. In non-limiting embodiments, for example, the compositions can comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, threonine, lysine, alanine, algae extract, *Aloe barbadensis, Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl ethylhexanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, proline, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, Macadamia ternifolia nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquatemium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCL, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers.

Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, hydroxypropyl cyclodextrin, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds include silicone oils such as a polyorganosiloxane. Non-limiting examples of polyorganosiloxanes include dimethicone, cyclomethicone, cyclohexasiloxane, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan g. Exfoliating Agent Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerythritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

In Vitro Activities

B16 Melanogenesis Assay: Each of the extracts identified in below Table 1 were subjected to a B16 pigmentation assay. This assay measure the ability of a given substance (plant extracts in the present case) to reduce the activity of melanogenesis in skin cells. In particular, melanogenesis is the process by which melanocytes produce melanin, a naturally produced pigment that imparts color to skin, hair, and eyes. Inhibiting melanogenesis is beneficial to prevent skin darkening and lighten dark spots associated with aging. The B16 pigmentation bioassay utilized B16-F1 melanocytes (ATCC), an immortalized mouse melanoma cell line, to analyze the effect of the plant extracts identified in Table 1 on melanogenesis. The endpoint of this assay was a spectrophotometric measurement of melanin production and cellular viability. B16-F1 melanocytes were cultivated in standard DMEM growth medium with 10% fetal bovine serum (Mediatech) at 37° C. in 10% $CO_2$ and then treated with the extracts in the concentration amounts indicated in Table 1 for 6 days. Following incubation, melanin secretion was measured by absorbance at 405 nm and cellular viability was quantified. It was shown that a super critical $CO_2$ extract of *Schinus terebinthifolius* seed (supplied by Barnet Products Corporation under the trade name ADIPOLIN™) inhibited melanin production by 35% at a concentration of 1 wt. %. Additionally, it was shown that a combination of aqueous extracts from *Ptychopetalum olacoides* bark/stem, *Pfaffia paniculata* root, and *Trichilia catigua* bark (supplied by Chemyunion under the trade name SLIMBUSTER™ H) inhibited melanin production by 17% at a concentration of 0.05 wt. % and by 42% at a concentration of 0.3 wt. %. It was also shown that a combination of aqueous extracts from the whole algae plants of *Himanthalia elongata* extract and *Undaria pinnatifida* extract (supplied by Biosil Technologies, Inc., under the trade name SLENDYL®) inhibited melanin production by 12% at a concentration of 2 wt. % and inhibited melanin production by 24% at a concentration of 3 wt. %.

Melanoderms (MatTek) Assay: The melanoderm (MatTek) assay measures the ability of a given substance (plant extracts in the present case) to inhibit melanin synthesis on melanoderm models. MatTek's MelanoDerm System consists of normal, human-derived epidermal keratinocytes (NHEK) and melanocytes (NHM) cultured to form a multilayered, highly differentiated model of the human epidermis. The NHM undergo melanogenesis leading to tissue pigmentation. Melanoderms were treated with 0.1 wt. % of super critical $CO_2$ *Schinus terebinthifolius* seed extract (supplied by Barnet Products Corporation under the trade name ADIPOLIN™), which produced a 40% reduction in pigmentation of the model. Melanoderms were also treated with 0.05 wt. % of a combination of aqueous extracts from *Ptychopetalum olacoides* bark/stem extract, *Pfaffia paniculata* root extract, and *Trichilia catigua* bark extract (supplied by Chemyunion under the trade name SLIMBUSTER™ H), which produced a 17% reduction in pigmentation of the model. Melanoderms were also treated with 2.0 wt. % of a combination of aqueous extracts from the whole algae plants of *Himanthalia elongata* and *Undaria pinnatifida* (supplied by Biosil Technologies, Inc., under the trade name SLENDYL®), which produced a 12% reduction in pigmentation of the model. Table 2 provides a summary of these data.

TABLE 2

(Melanoderm MatTek Data)

| Ingredient | Inhibition of melanin production (%) |
| --- | --- |
| *Schinus terebinthifolius* seed extract (ADIPOLIN ™) | 40% (at 0.1 wt. %) |
| *Ptychopetalum olacoides* bark/stem extract, *Pfaffia paniculata* root extract, and *Trichilia catigua* extract (SLIMBUSTER ™ H) | 17% (at 0.05 wt. %) |
| *Himanthalia elongata* extract, and *Undaria pinnatifida* extract (SLENDYL ®) | 12% (at 2.0 wt. %) |

Adiponectin Expression Assay: Human subcutaneous pre-adipocytes were cultured in 96-well plates and allowed to differentiate in the absence of the tested plant extracts. Three days prior to treatment with the plant extracts identified below in Table 3, the cells were rested in Basal Medium, thereby removing all serum and hormones from the cells. The cells were maintained in a 37° C. humidified incubator at 5% $CO_2$. Subsequently, the cells were treated with the plant extracts and controls in Adipocyte Medium for 72 hours, again maintained in a 37° C. humidified incubator at 5% $CO_2$. At the end of the treatment period, conditioned media was collected and stored at −800° C. until ready to assay. The secreted adiponectin was assayed using our Human Adiponectin ELISA Kit. 20 µl of thawed conditioned medium was removed and prepared for the ELISA. The final dilution of conditioned media in the ELISA was 25 fold. The

TABLE 1

(B16 Melanogenesis Data)

| Ingredient | Inhibition of melanin production (%) |
| --- | --- |
| *Schinus terebinthifolius* seed extract (ADIPOLIN ™) | 35% (at 1 wt. %) |
| *Ptychopetalum olacoides* bark/stem extract, *Pfaffia paniculata* root extract, and *Trichilia catigua* bark extract (SLIMBUSTER ™ H) | 17% (at 0.05 wt. %)<br>42% (at 0.3 wt. %) |
| *Himanthalia elongata* extract and *Undaria pinnatifida* extract (SLENDYL ®) | 12% (at 2 wt. %)<br>24% (at 3 wt. %) | absorbance of the plate was read at 450 nm. The unknown concentration of the test samples are calculated using the absorbance values of the adiponectin standard solutions assayed at the same time. As illustrated in Table 3, treatment with 1.0 wt. % of a super critical $CO_2$ extract of *Schinus terebinthifolius* seed (supplied by Barnet Products Corporation under the trade name ADIPOLIN™) resulted in a 29% increase in adiponectin secretion when compared with the control. Treatment with 1.0 wt. % of a combination of aqueous extracts of *Ptychopetalum olacoides* bark/stem, *Pfaffia paniculata* root, and *Trichilia catigua* bark (supplied by Chemyunion under the trade name SLIMBUSTER™ H) resulted in a 74% increase in adiponectin secretion when compared with the control.

TABLE 3

(Adiponectin Expression Data)

| Ingredient | Increase in adiponectin secretion (%) |
|---|---|
| *Schinus terebinthifolius* seed extract (ADIPOLIN ™) | 29% (at 1.0 wt. %) |
| *Ptychopetalum olacoides* bark/stem extract, *Pfaffia paniculata* root extract, and *Trichilia catigua* extract (SLIMBUSTER ™ H) | 74% (at 1.0 wt. %) |

Example 2

Clinical Efficacy Study

The combination of plant based materials selected from *Schinus terebinthifolius* seed extract, *Ptychopetalum olacoides* bark/stem extract, *Pfaffia paniculata* root extract, *Trichilia catigua* extract, *Himanthalia elongata* extract, and/or *Undaria pinnatifida* extract can be tested in a clinical study to determine the effectiveness of these compositions in clinical tests such as skin lightness and skin redness as measured by chromameter, reduction in mottled pigmentation as scored by a dermatologist, increase in skin radiance, skin firmness, and elasticity as scored in a clinician evaluation, reduction in overall photodamage as scored in a clinician evaluation, and increase in skin tone evenness as scored in a clinician evaluation. Additional tests can include level of erythema, redness, dryness, peeling, flaking, irritation, burning, stinging, itching, or tingling as self-scored by the clinical study participants. These results are expected to demonstrate that the benefits of use the combination of ingredients may act synergistically or that a combination of *Schinus terebinthifolius* seed extract, *Ptychopetalum olacoides* bark/stem extract, *Pfaffia paniculata* root extract, *Trichilia catigua* extract, *Himanthalia elongata* extract, and/or *Undaria pinnatifida* extract can be an effective substitute for hydroquinone, while avoiding unwanted side effects. Hydroquinone is a compound often used in skin lightening cosmetics and the treatment of pigmentation disorders. Some potential unwanted side effects of hydroquinone can include exogenous ochronosis (a pigmentation disorder characterized by blue-black pigmentation), confetti leucoderma (a pigmentation disorder characterized by confetti-like lesions), irritant reactions, and allergic reactions.

A randomized, controlled, double-blind clinical study can be performed to evaluate the tolerability and efficacy of one or more skin treatment products to lighten skin, even out skin tone, or treat hyperpigmentation. One such study could take place over the course of nine (9) weeks, wherein the first week can be a "wash-out" to ensure previous product usage by participants does not affect this study and the next eight weeks can include test product usage. The trial can include the use of one or more test products containing either a combination of *Schinus terebinthifolius* seed extract, *Ptychopetalum olacoides* bark/stem extract, *Pfaffia paniculata* root extract, *Trichilia catigua* extract, *Himanthalia elongata* extract, and *Undaria pinnatifida* extract (provided to approximately half the participants or one-third of the participants in a study including a placebo), a positive control or comparative product containing hydroquinone (provided to approximately half the participants or one-third of the participants in a study including a placebo), and/or a placebo (provided to approximately one-third of the participants in a study if the study includes a placebo). The clinical study can include supplemental products used by all participants.

Evaluation of skin for improvements in lightness of skin, skin tone evenness, and hyperpigmentation can be performed at the Baseline, Week 2, Week 4, and Week 8 of treatment. Additionally or alternatively, evaluation for improvements in skin for these factors can be performed at Week 1, Week 3, Week 5, and Week 7. Methods for evaluation can include a board-certified dermatologist evaluation for tolerance, expert clinical evaluation for efficacy, and chromameter for lightness in skin. The scores can be compared as the clinical study progresses and against hydroquinone or another tested product.

Participants can be chosen from healthy volunteers, including those aged 35 to 70 years, with a maximum of two participants aged 66 to 70 per treatment group. Participants can have Fitzpatrick skin types I to III (I—Always burns easily, never tans; II—Always burns easily, tans minimally; and III—Burns moderately, tans gradually), and can be regular users of facial cleansing and moisturizing products in their skin care routine. Participants should be tested at Screening and Baseline visits and scored moderate severity, or 4 to 6 on a 0 to 9 scale, for facial pigmentation.

Participants can be instructed to perform a morning routine and/or an evening routine using the test products. The morning routine can include applying facial cleanser and then applying test product to the entire face and forehead or to darker areas of the skin each morning for the duration of the study. The evening routine can include applying a facial cleanser and applying a "pea-sized" amount of the test product to the entire face and forehead or to darker areas of the skin, avoiding the eye area. For Weeks 0 to 2, participants can be instructed to apply the test product with a different frequency than the other weeks of the clinical study, e.g., performing the morning routine every other day as opposed to every day for Weeks 3 to 8.

Scores and data relating to the clinical tests can be collected and compared for the duration of the clinical study including chromameter scores for skin lightness and skin redness, dermatologist or clinician evaluations of reduction in mottled pigmentation, clinician evaluations for increase in skin radiance, skin firmness, and elasticity, clinician evaluations for reduction in overall photodamage in skin, and clinician evaluations for the increase in skin tone evenness. Scores can be compared to Baseline measurements and compared to the use of hydroquinone for skin lightening or pigmentation disorder treatment.

Dermatologist Tolerance tests can also be performed. These scores can be collected at the Baseline and end of Week 2, Week 4, and Week 8. Additionally or alternatively, these scores can be collected at the end of Week 1, Week 3, Week 5, and Week 7. The Dermatologist Tolerance scores can be scored on a scale from 0 to 3, with 0 being no effect ("none"), 1 being mild effect, 2 being a moderate effect ("Mod"), and 3 being a severe effect. Dermatologist Tolerance can be measured for erythema/redness, dryness, peeling/flaking, and irritation in skin and the scores can be compared as the clinical study progresses and against hydroquinone or another tested product.

Tolerance as experienced by the participant is also an important metric for comfort and ease of use, so Self-Assessment Tolerance can also be recorded. These scores can be collected at the Baseline and end of Week 2, Week 4, and Week 8. Additionally or alternatively, these scores can be collected at the end of Week 1, Week 3, Week 5, and Week 7. The Self-Assessment Tolerance scores can be scored on a scale from 0 to 3, with 0 being no effect ("none"), 1 being mild effect, 2 being a moderate effect ("Mod"), and 3 being a severe effect. Self-Assessment Tolerance can be measured for burning, stinging, itching, and tingling sensations in skin and the scores can be compared as the clinical study progresses and against hydroquinone or another tested product.

Example 3

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition can be compared with that of kojic acid (Sigma).

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Collagen Stimulation Assay: Collagen is an extracellular matrix protein critical for skin structure. Increased synthesis of collagen helps improve skin firmness and elasticity. This bioassay can be used to examine the effects on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide is pre-coated onto a microplate. Standards and samples are pipetted into the wells and any procollagen peptide present is bound by the immobilized antibody. After washing away any unbound substances, an enzyme-linked polyclonal antibody specific for procollagen peptide is added to the wells. Following a wash to remove any unbound antibody-enzyme reagent, a substrate solution is added to the wells and color developed in proportion to the amount of procollagen peptide bound in the initial step. Color development is stopped and the intensity of the color at 450 nm can be measured using a microplate reader.

For generation of samples and controls, subconfluent normal human adult epidermal fibroblasts (Cascade Biologics) can be cultivated in standard DMEM growth medium with 10% fetal bovine serum (Mediatech) at 37° C. in 10% $CO_2$. The cells are treated with each of the tested ingredients and controls for 3 days. Following incubation, cell culture medium is collected and the amount of procollagen peptide secretion is quantified using the sandwich enzyme linked immuno-sorbant assay (ELISA) from Takara (#MK101) as explained above.

Antioxidant (AO) Assay: An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®•+by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Michigan USA) can be used as an in vitro bioassay to measure the total anti-oxidant capacity of each of any one of the active ingredients, combination of ingredients, or compositions having said combinations disclosed in the specification. The protocol can be followed according to manufacturer recommendations.

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Matrix Metalloproteinase 3 and 9 Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M−1cm−1 at pH 6.0 and above 7). The active ingredients, any one of the combination of ingredients, or compositions having said combinations disclosed in the specification can be assayed.

Matrix Metalloproteinase 1 Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygenase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachidonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoyganse activity can be calculated compared to non-treated controls to determine the ability of each of the active ingredients, any one of the combination of ingredients, or compositions having said combinations disclosed in the specification to inhibit the activity of purified enzyme.

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers can be monitored in cultured human fibroblasts by staining of cultured human fibroblasts using immunofluorescent antibodies directed against elastin.

Laminin and Fibronectin Stimulation Assay: Laminin and fibronectin are major proteins in the dermal-epidermal junction (DEJ) (also referred to as the basement membrane). The DEJ is located between the dermis and the epidermis and interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal cells to the DEJ. Laminin and fibronectin secretion can be monitored by quantifying laminin and fibronectin in cell supernatants of cultured human fibroblasts treated for 3 days with culture medium with or without the test ingredient(s). Following incubation, laminin and fibronectin content can be measured using immunofluorescent antibodies directed against each protein in an enzyme linked immuno-sorbant assay (ELISA). Measurements are normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color developed in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EPILIFE™ standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Elastase Assay: ENZCHEK® Elastase Assay (Kit #E-12056) from Molecular Probes (Eugene, Oregon USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations can be made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200—Mattek EPIL-IFE™ growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin: Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% CO2 for 24 hours in EPILIFE™ growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in EPILIFE™ growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Production of Hyaluronic Acid: Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine array: Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 µl of 100× stock) and 0.1% (10 µl of 100× stock) test compositions are diluted into a final volume of 1 ml EPILIFE™ Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temp. using 70 ml S&S Protein Array Blocking buffer (Whatman Schleicher and Scheull). Blocking buffer is removed and 70 ml of each supernatant sample is added to each array. Arrays are incubated for 3 hours at room temp. with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temp. with gentle agitation. Arrays are washed 3 times with TBS-T. Arrays are incubated with 70 ml of a solution containing streptavidin-Cy5 conjugate for 1 hour at room temp. with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 μg/ml bovine brain extract, 1 μg/ml hydrocortisone, and 1 μg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 μl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for reducing melanin in hyperpigmented skin in a person, wherein the hyperpigmented skin is caused by increased melanin production, the method comprising topically applying to hyperpigmented skin caused by increased melanin a composition comprising:

0.0001 wt. % to 1 wt. % of a mixture comprising a combination of *Ptychopetalum olacoides* bark/stem extract obtained by aqueous extraction and comprising water soluble components of *Ptychopetalum olacoides* bark/stem, *Pfaffia paniculata* root extract obtained by aqueous extraction and comprising water soluble components of *Pfaffia paniculata* root, and *Trichilia catigua* bark extract obtained by aqueous extraction and comprising water soluble components of *Trichilia catigua* bark;

wherein topical application of the composition reduces melanin in the hyperpigmented skin.

2. The method of claim 1, wherein the hyperpigmented skin is a senile lentigo, or melasmic skin, or both.

3. The method of claim 1, wherein the composition whitens the skin, or evens out the skin tone, or both.

4. The method of claim 1, wherein the composition reduces melanogenesis activity in the skin.

5. The method of claim 1, wherein the composition reduces melanogenesis activity through activation of an adiponectin receptor.

6. The method of claim 5, wherein the adiponectin receptor is PAQR7.

7. The method of claim 1, wherein the mixture further comprises water, butylene glycol, and PEG-40 hydrogenated castor oil.

8. The method of claim 1, wherein the composition comprises
0.0001 to 0.5% w/w of the mixture comprising the combination of the *Ptychopetalum olacoides* bark/stem extract, the *Pfaffia paniculata* root extract, and the *Trichilia catigua* bark extract.

9. The method of claim 1, wherein the composition is an emulsion.

10. The method of claim 1, wherein the composition is a gel.

* * * * *